United States Patent
Bellamkonda et al.

(10) Patent No.: US 11,273,250 B2
(45) Date of Patent: Mar. 15, 2022

(54) DEVICES, SYSTEMS, AND METHODS FOR EXCAVATING CANCER CELLS

(75) Inventors: Ravi V. Bellamkonda, Marietta, GA (US); Anjana Jain, Worcester, MA (US); Nassir Mokarram-Dorri, Durham, NC (US); Barun Brahma, Atlanta, GA (US)

(73) Assignees: GEORGIA TECH RESEARCH CORPORATION, Atlanta, GA (US); CHILDREN'S HEALTHCARE OF ATLANTA, INC., Atlanta, GA (US)

( * ) Notice: Subject to any disclaimer, the term of this patent is extended or adjusted under 35 U.S.C. 154(b) by 349 days.

(21) Appl. No.: 13/814,009

(22) PCT Filed: Aug. 4, 2011

(86) PCT No.: PCT/US2011/046653
§ 371 (c)(1),
(2), (4) Date: Feb. 28, 2013

(87) PCT Pub. No.: WO2012/019049
PCT Pub. Date: Feb. 9, 2012

(65) Prior Publication Data
US 2013/0172846 A1  Jul. 4, 2013

Related U.S. Application Data

(60) Provisional application No. 61/370,630, filed on Aug. 4, 2010.

(51) Int. Cl.
*A61M 5/00* (2006.01)
*A61K 9/70* (2006.01)
(Continued)

(52) U.S. Cl.
CPC ............. *A61M 5/00* (2013.01); *A61K 9/0092* (2013.01); *A61K 9/70* (2013.01); *A61K 31/05* (2013.01);
(Continued)

(58) Field of Classification Search
None
See application file for complete search history.

(56) References Cited

U.S. PATENT DOCUMENTS 4,552,707 A   11/1985  How
4,892,552 A    1/1990  Ainsworth et al.
(Continued)

FOREIGN PATENT DOCUMENTS

JP   2008536539 A    9/2008
WO  2008137659 A1  11/2008
(Continued)

OTHER PUBLICATIONS

Campbell et al, Differential toxicity of aluminum salts in human cell lines of neural origin: implications for neurodegeneration, 2001, NeuroToxicology, 22: 63-71.*
(Continued)

*Primary Examiner* — Sharmila G Landau
*Assistant Examiner* — Stephanie A McNeil
(74) *Attorney, Agent, or Firm* — Benesch, Friedlander, Coplan & Aronoff LLP

(57) ABSTRACT

Methods, devices, and systems are provided for guiding tumor movement, particularly in vivo for treatment of patients. The method may include implanting into a tissue site where tumor cells are present a device having one or more surface structures or substrates, such as aligned nanofibers, which provide physical guidance cues for directing the migration of the tumor cells from the first tissue location to a selected second location, for tumor cell extraction or
(Continued)

death. The devices and systems may include a cytotoxic agent for contacting tumor cells migrated via the substrate. All or a portion of the at least one substrate may include one or more biochemical cues, such as a coating of laminin or another protein, which may be provided in a concentration gradient to facilitate uni-directional tumor cell migration.

13 Claims, 6 Drawing Sheets

(51) Int. Cl.
| | |
|---|---|
| A61K 9/00 | (2006.01) |
| A61K 31/4355 | (2006.01) |
| A61K 31/443 | (2006.01) |
| A61K 47/34 | (2017.01) |
| A61K 31/704 | (2006.01) |
| A61K 31/05 | (2006.01) |
| A61L 31/16 | (2006.01) |
| A61L 31/06 | (2006.01) |
| A61L 31/10 | (2006.01) |
| A61K 47/64 | (2017.01) |
| A61K 47/59 | (2017.01) |

(52) U.S. Cl.
CPC ........ *A61K 31/4355* (2013.01); *A61K 31/443* (2013.01); *A61K 31/704* (2013.01); *A61K 47/34* (2013.01); *A61K 47/593* (2017.08); *A61K 47/6435* (2017.08); *A61L 31/06* (2013.01); *A61L 31/10* (2013.01); *A61L 31/16* (2013.01); *A61L 2300/416* (2013.01); *A61L 2400/12* (2013.01)

(56) References Cited

U.S. PATENT DOCUMENTS

| | | | |
|---|---|---|---|
| 5,053,453 | A | 10/1991 | Ku |
| 5,217,492 | A | 6/1993 | Guire et al. |
| 5,916,585 | A | 6/1999 | Cook et al. |
| RE36,370 | E | 11/1999 | Li |
| 6,303,136 | B1 | 10/2001 | Li et al. |
| 6,309,423 | B2 | 10/2001 | Hayes |
| 6,347,930 | B1 | 2/2002 | Muscat et al. |
| 6,716,225 | B2 | 4/2004 | Li et al. |
| 7,214,242 | B2 | 5/2007 | Abraham et al. |
| 7,374,774 | B2 | 5/2008 | Bowlin et al. |
| 7,481,788 | B2 | 1/2009 | Naimark et al. |
| 7,531,503 | B2 | 5/2009 | Atala et al. |
| 7,615,373 | B2 | 11/2009 | Simpson et al. |
| 7,622,299 | B2 | 11/2009 | Sanders et al. |
| 7,704,740 | B2 | 4/2010 | Schindler et al. |
| 2003/0017141 | A1 | 1/2003 | Poznansky et al. |
| 2003/0175410 | A1 | 9/2003 | Campbell |
| 2003/0211130 | A1 | 11/2003 | Sanders et al. |
| 2004/0037813 | A1 | 2/2004 | Simpson et al. |
| 2004/0052861 | A1 | 3/2004 | Hatcher |
| 2005/0038498 | A1 | 2/2005 | Dubrow et al. |
| 2005/0095695 | A1 | 5/2005 | Shindler et al. |
| 2005/0187162 | A1 | 8/2005 | Dhanaraj et al. |
| 2006/0085063 | A1 | 4/2006 | Shastri et al. |
| 2007/0269481 | A1 | 11/2007 | Li et al. |
| 2008/0208358 | A1 | 8/2008 | Bellamkonda et al. |
| 2008/0220042 | A1 | 9/2008 | Hashi et al. |
| 2009/0043380 | A1* | 2/2009 | Blaha ............... A61L 31/10 623/1.46 |
| 2009/0082856 | A1 | 3/2009 | Flanagan |
| 2010/0129418 | A1 | 5/2010 | Lawrence et al. |
| 2010/0159008 | A1* | 6/2010 | Barron et al. ............... 424/484 |
| 2010/0211172 | A1 | 8/2010 | Bellamkonda et al. |
| 2010/0273258 | A1 | 10/2010 | Lannutti et al. |
| 2011/0038936 | A1 | 2/2011 | Griswold et al. |

FOREIGN PATENT DOCUMENTS

| | | |
|---|---|---|
| WO | 2009002401 A2 | 12/2008 |
| WO | 2011032139 A2 | 3/2011 |

OTHER PUBLICATIONS

Hoek et al, Ethanol, oxidative stress, and cytokine-induced liver cell injury, 2002, Alcohol 27: 63-68.*

Bar et al, Cyclopamine-Mediated Hedgehog Pathway Inhibition Depletes Stem-Like Cancer Cells in Glioblastoma, 2007, Stem Cells, 25(10): 2524-2533.*

Xiong, Size influences the cytotoxicity of poly (lactic-co-glycolic acid) (PLGA) and titanium dioxide (TiO2) nanoparticles, 2013, Arch Toxicol 87:1075-1086.*

Bini et al., "Peripheral Nerve Regeneration by Microbraided Poly (L-lactide-co-glycolide) Biodegradable Polymer Fibers." Journal of Biomedical Materials Research A, 2003, pp. 286-305, vol. 68.

Clements et al., "Thin-film enhanced nerve guidance channels for peripheral nerve repair." Biomaterials, 2009, pp. 3834-3846, vol. 30, Issue 23-24.

Dubey et al., "Guided Neurite Elongation and Schwann Cell Invasion into Magnetically Aligned Collagen in Simulated Peripheral Nerve Regeneration." Experimental Neurology, 1999, pp. 338-350, vol. 158.

Hatton, Paul V., "Tissue Engineering of Human Cartilage-Spider Silk and other Scaffolds." Centre for Biomaterial and Tissue Engineering at the University of Sheffield. From molecules to patients conference, Jun. 9, 2005 <http://www.cbte.group.shef.ac.uk/news/abstracts/hatton/html> (abstract).

He et al., "Fabrication of Collagen-Coated Biodegradable Polymer Nanofiber Mesh and its Potential for Endothelial Cells Growth." Biomaterials, 2005, pp. 7606-7615, vol. 26, pp. 7606-7615, Abstract, Section 3.1, figures.

Jha et al., "Electrospun Collagen: A Tissue Engineering Scaffold with Unique Functional Properties in a Wide Variety of Applications." Journal of Nanomaterials, 2011, pp. 1-15, vol. 2011.

Johnson et al., Quantitative Analysis of Complex Glioma Cell Migration on Electrospun Polycaprolactone Using Time-Lapse Microscopy, Tissue Engineering: Part C, 2009, pp. 531-540, vol. 15, Issue 4.

Kim et al., "The role of aligned polymer fiber-based constructs in the bridging of long peripheral nerve gaps", Biomaterials, 2008, pp. 3117-3127, vol. 29.

Li et al., "Electrospinning Nanofibers as Uniaxially Aligned Arrays and Layer-by-Layer Stacked Films." Advanced Materials, 2004. pp 361-66, vol. 16, Issue 4.

Li et al., "Nanofiber Scaffolds with Gradations in Mineral Content for Mimicking the Tendon-to-Bone Insertion Site, Nano Letters." 2009, pp. 2763-2768, vol. 9, Issue 7.

Ma et al. "Grafting of gelatin on electrospun poly(caprolactone) nanofibers to improve endothelial cell spreading and proliferation and to control cell orientation", Tissue Engineering, Jul.-Aug. 2005, pp. 1149-1158, vol. 11, Issue 7-8.

Ma, Peter X., "Polymeric Biomaterials and Tissue Engineering Lab.".

Ngo et al., "Poly (•-lactide) Microfilaments Enhance Peripheral Nerve Regeneration Across Extended Nerve Lesions." Journal of Neuroscience Research 2003, pp. 227-238, vol. 72.

Oest et al., "Oriented Porous Polymer Scaffolds Promote Vascularized Repair of Critically-Sized Bone Defects in Vivo." Regenerate, Jun. 1-3, 2005 <http://www.regenerate-online.com/abstract_Oest.html> (abstract).

Rangappa et al., "Laminin-coated Poly (L-lactide) Filaments Induce Robust Neurite Growth While Providing Directional Orientation." Journal of Biomedical Materials Research A, 2000, pp. 625-634, vol. 51.

"Scaffolds for Developing 3D Tissues." Centre for Biomaterial and Tissue Engineering at the University of Sheffield. <http://www.cbte.group.shef.ac.uk/research/mat5.html>, retrieved on Jan. 10, 2006.

(56) References Cited

OTHER PUBLICATIONS

Schwall et al., "Micro- and Nanoscale Hydrogel Systems for Drug Delivery and Tissue Engineering." Materials, 2009, pp. 577-612, vol. 2.
Stang et al., "Collagen nerve conduits-assessment of biocompatibility and axonal regeneration." Bio-medical materials and engineering, 2005, pp. 3-12, vol. 15, Issue 1-2.
Xie et al., "Electrospun Micro- and Nanofibers for Sustained Delivery of Paclitaxel to Treat C6 Glioma in Vitro, Pharmaceutical Research." Aug. 2006, pp. 1817-1826, vol. 23 Issue 8.
Xu et al., "Aligned Biodegradable Nanofibrous Structure: A Potential Scaffold for Blood Vessel Engineering." Biomaterials, 2004, pp. 877-886, vol. 25, Issue 5.
Yang, F. et al. "Electrospinning of nano/micro scale poly(•-lactic acid) aligned fibers and their potential in neural tissue engineering", Biomaterials, 2005, pp. 2603-2610, vol. 26, No. 15.
European Search Report issued in European U.S. Appl. No. 17/199,344 dated Dec. 19, 2017.
Johnson et al., "Quantitative Analysis of Complex Glioma Cell Migration on Electrospun Polycaprolactone Using Time-Lapse Microscopy," Tissue Engineering Part C, vol. 15 pp. 531-540.
Xie & Wang, "Electrospun Micro- and Nanofibers for Sustained Delivery of Paclitaxel to Treat C6 Glioma in Vitro," Pharmaceutical Research 23(8):1817-25 (2006).
First Examination Report of European Patent Application No. 11815346.9—dated Jun. 29, 2015.
Office Action of Japanese Patent Application No. 2013-523347 dated Jun. 23, 2015.

* cited by examiner

DEVICES, SYSTEMS, AND METHODS FOR EXCAVATING CANCER CELLS

CROSS-REFERENCE TO RELATED APPLICATIONS

The present application is a national phase entry of PCT Patent Application No. PCT/US2011/046653, filed on Aug. 4, 2011, designating the United States of America, and claims the benefit of U.S. Provisional Application No. 61/370,630, filed Aug. 4, 2010. The applications are incorporated herein by reference.

BACKGROUND

The present application relates to implantable medical devices, systems, and methods for treatment of cancer. In particular, the present application relates to systems and methods for directing cancer cell migration in order to remove, relocate, or manage the growth of tumors, including tumors that would otherwise be inoperable or lead to a recurrence of the tumor.

Medulloblastomas are highly invasive tumors of the cerebellum and the most common childhood malignant brain tumor, constituting 20-40% of all pediatric brain tumors. Treatment of these invasive intracranial brain tumors in children provides significant challenges that are further complicated by the confined space and need to preserve as much non-cancerous, "normal" tissue as possible to avoid long-term cognitive dysfunction. In such cases, surgery is complicated and chemotherapy is prone to major side effects because cyclototoxic drugs cannot differentially kill invading tumor cells surrounded by normal cells.

Malignant gliomas also are among the most aggressive and least successfully treated types of cancer, with few patients surviving longer than a year following diagnosis. This bleak prognosis is largely attributed to the uniquely invasive ability of gliomas cells to detach from the tumor mass, infiltrate normal brain tissue, evade immunodetection and resist normally cytotoxic therapies. The invasion of these tumors prevents complete surgical removal and contributes to recurrence and a rapid, lethal outcome.

Studies have shown that the invasion of malignant gliomas predominantly occurs along major elongated structures, such as white matter fiber tracts and blood vessels, which act as "highways" for the spread of these tumors. It is generally believed that the myelin along the white matter fiber tracts aids with the adhesion and migration of the glioma cells. In addition, other proteins in the basement membrane have been implicated in association with migration along the blood vessels.

Accordingly, there remains a need to develop an alternative treatment for medulloblastomas and other malignancies, such as malignant gliomas.

BRIEF DESCRIPTION OF THE DRAWINGS

FIG. 2A illustrates a tubular conduit with an aligned nanofiber film conduit while FIG. 2B illustrates a tubular conduit having a spiral aligned nanofiber film.

FIGS. 7B and 7E show live tumor cells stained with calcein. FIGS. 7C and 7F show dead tumor cells stained with ethidium homodimer.

SUMMARY

Figure 1:
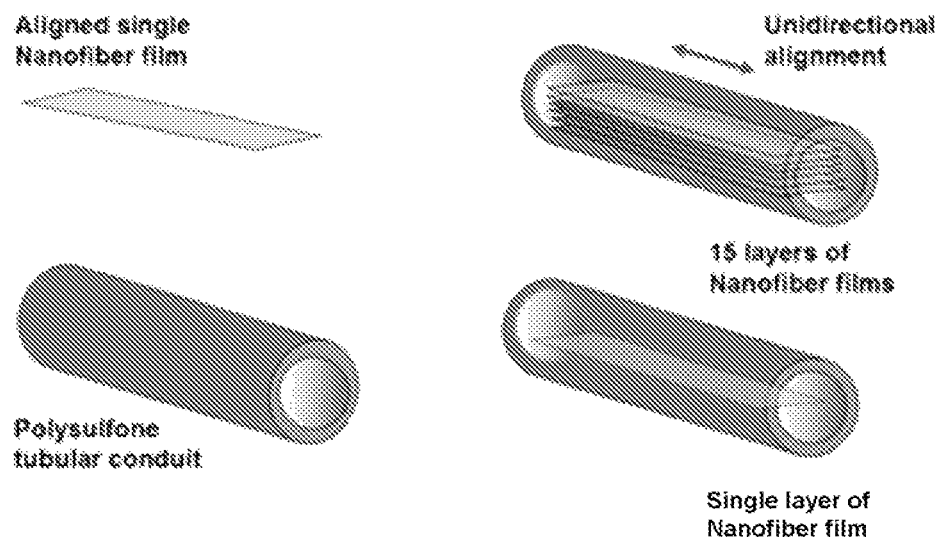
FIG. 1 is a schematic shoving different embodiments of an implantable system that includes a substrate with a film of a plurality of aligned nanofibers.

One embodiment of the present description includes an implantable system for promoting tumor cell migration for cell removal or death. The system comprises at least one substrate having a surface configured to provide cues for directing tumor cell migration along the substrate surface, the at least one substrate comprising a plurality of aligned nanofibers. Desirably, the system further comprises at least one cytotoxic agent for contacting tumor cells migrated via the at least one substrate.

In another aspect, an implantable device is provided for promoting tumor cell migration for cell removal or death. The device comprises at least one film having a surface configured to provide cues for directing tumor cell migration along the substrate surface, wherein the surface comprises a coating material gradient to effect uni-directional or bi-direction growth of cells across the surface.

In still another aspect, a method is provided for guiding tumor movement in vivo. The method comprises implanting into a tissue site were tumor cells are present a device having one or more surface structures which provide physical guidance cues for directing the migration of the tumor cells from the first tissue location to a selected second location.

In another aspect, a method is provided for treating a patient comprising implanting at a tissue site in the patient a device comprising a substrate having a surface configured to provide cues for directing tumor cell migration along the substrate surface, the substrate comprising a plurality of aligned nanofibers. The method further comprises subsequently killing or removing tumor cells that have migrated along the substrate surface.

DETAILED DESCRIPTION

Embodiments of the present description address the above-described needs by providing implantable devices and systems that offer migratory tumors an alternate, preferential pathway for migration—a pathway that ultimately leads to their death or removal. In particular, innovative implantable devices and systems are provided that advantageously exploit, the properties and mechanics of cell motility and migration characteristic of metastasis to manage growth of malignant tumors, particularly invasive malignant brain tumors. The implantable structures beneficially can be used to guide tumor extraction and tumor movement from one location (such as an inoperable location) to a secondary location (such as an operable location or cytotoxic sink).

In an embodiment, the implantable device for promoting tumor cell migration comprises a substrate having a surface configured to provide cues for directing tumor cell migration along the substrate surface. The implantable device desirably is sized and shaped so that it may be implanted at or near malignant tumors using minimally invasive techniques. In particular embodiments, the implantable devices provide an attractive alternative for migrating tumors cells; promote unidirectional migration of tumors; and provide a 'sink' to either collect, capture and/or kill the migrating tumor cells. In particular, the topographical or biochemical cues promote migration of the tumor cells into the implantable device while minimizing or eliminating diffusion of any such cues, thereby maintaining the stability of the primary tumor location and mitigating or avoiding any unintended contributions to tumor migration.

Embodiments of the present description generally comprise a substrate having a surface configured to provide physical and/or chemical cues for directing (guiding) tumor cell migration along the substrate surface. In various embodiments, the physical guidance cues include one or more of substrate topography features, such as grooves, and films comprised of arrays of nanofiber or microfiber, such as aligned nanofibers.

In addition to guiding such tumor movement by physical topographical guidance cues, the methods and devices described herein optionally may be used in combination with other guidance means, such as electric fields, chemoattractants, and cell seeding that may serve to modulate or enhance the tumor cell movement or extraction. Such other guidance means may be known in the art, although not applied in the context of tumor cell extraction or movement in vivo.

Figures 2A, 2B:
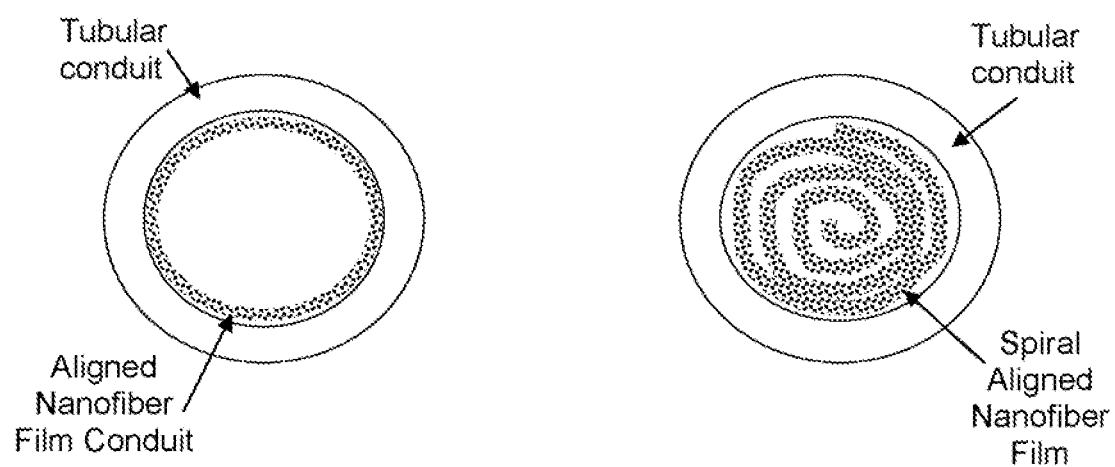
FIGS. 2A and 2B are cross-sectional views of a schematic of one embodiment of a tubular construct having a plurality of aligned nanofibers.

In a particular embodiment, the substrate comprises a plurality of aligned nanofibers. The plurality of aligned nanofibers may be in the form of a nanofiber film, a tubular construct, or any other suitable three-dimensional configuration. (See FIG. 1). In particular embodiments, the plurality of aligned nanofibers are in the form of a single nanofiber film disposed in a tubular construct (See FIGS. 1, 2A, and 2B). Such tubular constructs may, for example, provide structural support for the nanofiber films. Alternatively, the tubular construct can also contain two or more nanofiber films. The two or more films may be stacked on top of each other, optionally with a spacer material therebetween, to provide multiple surfaces on which the tumor cells may migrate. (See FIG. 1). In still other embodiments, the nanofiber films can be intricately designed such that one or more of the films can be inserted into the tumor and then converge at points outside the tumor where the cells migrate, and may be subsequently be removed or killed.

As used herein, the terms "nanofiber" refers to a fiber, strand, fibril, or threadlike structure having a diameter from about 40 nm to about 1500 nm. As used herein, the term "nanofilament" is synonymous with "nanofiber." In an embodiment, the nanofibers have a diameter from about 200 nm to about 1000 nm, from about 400 nm to about 1000 nm, from about 500 to about 800 nm, or from about 600 to about 800 nm.

In one embodiment in which the substrate surface comprises grooves that provide the physical cues for tumor cell migration. For example, the grooves may be dimensioned to be approximately the same width and approximately the depth, or half the depth, as the diameter the nanofibers.

Figure 1A:
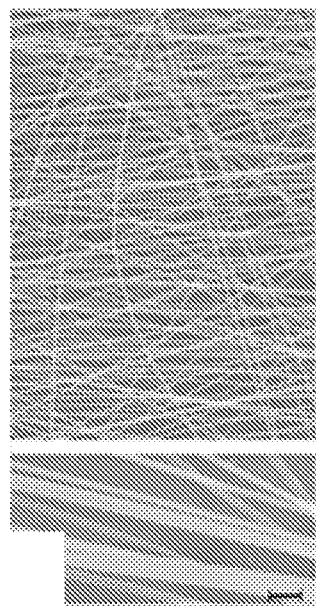
FIG. 1A are scanning electron micrograph images of uniaxially aligned nanofibers, with the magnified nanofibers having a scale bar=1 μm.

As used herein, the term "aligned nanofibers" refers to nanofibers having uniaxial orientation. As used herein, the term "uniaxial orientation" refers to a collection of nanofibers where greater than 50% of the nanofibers are oriented within 40 of an axis, i.e., ±20° of the axis. Importantly, the nanofibers are oriented in the structure over several millimeters in length, e.g., between 2 and 100 mm. In an embodiment, at least 60%, at least 75%, or at least 85%, of the nanofibers are within 20 degrees of the uniaxial orientation. Such uniaxially aligned nanofibers are illustrated in FIG. 1A.

As used herein, the term "implantable device" means that the device is suitable for use in vivo, i.e., by implantation into a patient in need of treatment, for example treatment of a malignant tumor, such as a medulloblastoma or metastatic glioma. In an embodiment, the device is used in the treatment of other types of malignances. The implantation site may be in the brain of the patient.

The nanofibers may be formed from at least one polymer using methods known in the art. The nanofibers may be composed of synthetic or natural polymers or a mixture of synthetic and natural polymers. The polymer may be biodegradable or nonbiodegradable, or may include a mixture of biodegradable and non-biodegradable polymers. In particular embodiments, the nanofibers desirably comprise a biodegradable synthetic polymer. For example, in an embodiment, the polymer is a biocompatible, thermoplastic polymer such as a polyester or polyamide suitable for use in in vivo applications in humans.

Representative examples of synthetic polymers include poly(hydroxy acids) such as poly acid), poly (glycolic acid), and poly(lactic acid-co-glycolic acid), poly (lactide), poly (glycolide), poly(lactide-co-glycolide), polyanhydrides, polyorthoesters, polyamides, polyalkylenes such as polyethylene and polypropylene, polyalkylene glycols such as poly (ethylene polyalkylene oxides such as poly(ethylene oxide), polyvinyl alcohols, polyvinyl ethers, polyvinyl esters, polyvinylpyrrolidone, poly(vinyl alcohols), poly(butyric acid), poly(valeric acid), and poly(lactide-cocaprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Exemplary biodegradable polymers include polymers of hydroxy acids such as lactic acid and glycolic acid, and copolymers with polyethylene glycol (PEG), polyanhydrides, poly(ortho)esters, poly(butyric add), poly(valeric acid), poly(lactide-co-caprolactone), blends and copolymers thereof. Desirably, the biodegradable polymer nanofibers include a poly(caprolactone), a poly (lactic-co-glycolic acid), a poly (aery lonitrile), or a combination thereof.

Representative examples of suitable natural polymers include proteins such as albumin, collagen, gelatin, Matrigel, fibrin, polypeptide or self-assembling peptide-based hydrogels, and prolamines, for example, zein, and polysaccharides such as alginate, agarose, cellulose and polyhydroxyalkanoates, for example, polyhydroxybutyrate.

The structure of the implantable device may include a film of uniaxially oriented nanofibers or a plurality of such films in a stack. (FIG. 1). In one embodiment, each film layer is about 10 μm thick. Thicker or thinner layers may also be used; however, the thickness typically is selected to be one capable of handling and manipulation to stack or otherwise assemble the implantable device. For example, the film thickness may enable manual handling, such as to facilitate separation from a mandrel or other (temporary) substrate on which the nanofibers are electrospun. In embodiments comprising a plurality of stacked nanofiber films, each layer may be oriented such that the nanofiber orientation in the stack is essentially the same (e.g., such that the axial direction of all layers is pointing in substantially the same direction) or such that the nanofiber orientation of each layer in the stack is offset (e.g., such that the axial direction of each layer is substantially perpendicular).

Optionally, the stacked structure includes a spacer between some or all of the layers of uniaxially oriented nanofiber films. The spacer may be water soluble or water insoluble, porous or non-porous, preferably is biocompatible, and may be bioerodible/biodegradable. The spacer may have a thickness between about 25 and about 800 μm. In an embodiment, each spacer layer in the stack has a thickness of about 50 to about 250 μm. In an embodiment, the spacer includes a hydrogel, such as a thermo-reversible (i.e., temperature responsive) hydrogel. In one embodiment, the structure consists of alternating layers of oriented nanofibers and layers of a hydrogel or other spacer. The hydrogel, for instance, may be an agarose hydrogel or other hydrogel known in the art. In other embodiments, the spacer material may be another gel or gel-like material, such as polyethylene glycol, agarose, alginate, polyvinyl alcohol, collagen. Matrigel, chitosan, gelatin, or combination thereof.

In an alternative embodiment, the uniaxially aligned nanofibers are provided in the structure in a form other than a plurality of layers. For example, the aligned nanofiber layers may be evenly spaced throughout the three-dimensional structure or a three-dimensional structure may be formed by rolling one layer, i.e. a film, of aligned nanofibers in on itself to form a tubular conduit (e.g., having an inner lumen, illustrated in FIG. 2A) or tubular scaffold (illustrated in FIG. 2B). The aligned nanofiber layers also may be engineered in any other suitable configuration to facilitate surgical implantation or minimally invasive implantation of the device at a location proximate to the tumor.

The nanofibers structure optionally may be disposed in a secondary structure for containing, positioning, or securing the uniaxially oriented nanofiber structure, and/or for further directing or limiting tumor cell growth. The secondary structure may also aid in shielding healthy tissues from contact with the migrating tumor cells.

In one embodiment, the secondary structure may be a tubular conduit, in which the nanofiber film(s) can be contained. This structure desirably also is made of a biocompatible polymer suitable for use in vivo. The polymer may be biodegradable or non-biodegradable, or a mixture thereof. In one embodiment, the secondary structure comprises a polysulfone, polycaprolactone, polyurethane, or PLGA. In a particular embodiment, the secondary structure is a tubular conduit made of polysulfone, poly caprolactone, polyurethane. PLGA, or a combination thereof. The secondary structure may be substantially flexible or rigid, depending upon its particular performance needs.

The nanofibers described herein may be made by essentially any technique known in the art. Desirably, the nanofibers are made using an electrospinning technique using essentially any biocompatible polymer that is amenable to electrospinning. The electrospinning equipment may include a rotating drum or other adaptation at the collector end to generate fibers oriented in the millimeter range.

In certain embodiments, the implantable devices provided herein further comprise biochemical cues to provide cues for directional migration of the tumor cells. For example, in embodiments the biochemical cue may comprise a coating of the plurality of uniaxially aligned nanofibers or nanofiber film with one or more bioactive agents capable of promoting directional migration of the tumor cells. Such coatings may be applied to the substrate using methods known to those skilled in the art, including, for example, nano-inkjet printing.

As used herein, the term "bioactive agent" refers to a molecule that exerts an effect on a cell or tissue. Representative examples of types of bioactive agents include therapeutics, vitamins, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, prostaglandins, immunoglobulins, cytokines, and antigens. Various combination of these molecules can be used. Examples of cytokines include macrophage derived chemokines, macrophage inflammatory proteins, interleukins, tumor necrosis factors. Examples of proteins include fibrous proteins (e.g., collagen, elastin) and adhesion proteins (e.g., actin, fibrin, fibrinogen, fibronectin, vitronectin, laminin, cadherins, selectins, intracellular adhesion molecules, and integrins). In various cases, the bioactive agent may be selected from fibronectin, laminin, thrombospondin, tenascin C, leptin, leukemia inhibitory factors, RGD peptides, antiTNFs, endostatin, angiostatin, thrombospondin, osteogenic protein-1, bone morphogenic proteins, osteonectin, somatomedin-like peptide, osteocalcin, interferons, and interleukins.

In particular embodiments, the bioactive agent comprises proteins, small molecules or biopolymers which have migration-promoting effects. Non-limiting examples of such bioactive agents include myelin or basement membrane proteins, such as laminin, collagen, and Matrigel. In embodiments, the bioactive agent comprises different proteins and molecules that are attractive to various tumor cells. In other aspects, the bioactive agent comprises charged elements such as polylysine or biopolymers, such as chitosan, capable of promoting migration of tumor cells away from the tumor in a directed manner.

In embodiments, the above-described biochemical cues may be applied to the plurality of nanofibers uniformly or in a gradient. Such gradients may be increasing or decreasing in the concentration or mass of the bioactive agent per given area. (See FIG. 4). In certain embodiments, the gradient aids in promoting one-directional migration of the rumor cells. In another embodiment, the gradient promotes bi-directional migration of cells. For instance, the gradient may comprise a higher concentration in one direction and a lower concentration in another direction to promote migration of two different cell types in opposite directions. Such bi-directional promoting gradients could limit tumor cell migration in one direction along the plurality of nanofibers away from the tumor site, while promoting migration of other cell types to the tumor site. Not wishing to be bound by any theory, it is believed that by migration of non-tumor cells to the tumor site, such as cells that elicit immune system sensitivity in tumors, could function to direct a natural immune response to the tumors. In certain embodiments, the immune-promoting cells could be genetically altered to remove the immune privilege status of the tumor.

Although the foregoing embodiments describe the preferred use of nanofibers, those skilled in the art should appreciate that the embodiments of the implantable devices provided herein also may be prepared using other types of materials engineered to promote directional migration of the tumor cells. Thus, in particular embodiments non-nanofiber based substrates may be used to induce migration of tumor cells in a desired direction to a desired location. For example, gradients of bioactive agents can be created in other materials, such as hydrogels and polymeric films, along with other directional cues that may or may not be based on topographical guidance of cells from the tumor to a region where the cells may be killed or removed.

The implantable devices desirably further comprise a cytotoxic agent. The cytotoxic agent may be tethered or conjugated directly to the plurality of nanofibers or a polymeric 'sink'. (See FIG. 3).

As used herein, "cyctoxic agent" means an apoptosis-inducing drug capable of inducing programmed cell death of tumor cells. In embodiments, the cytotoxic agent can be specific to a mutated signaling pathway that caused the tumor growth. In other embodiments, the cytotoxic agent can be a drug that is cytotoxic to any cells but which the conjugation of the prevents healthy normal cells from being affected. In various examples, the cytotoxic agent may include cyclopamine, honokiol, furegrelate, doxorubicin, or a combination thereof. In one embodiment, the cytotoxic agent comprises cyclopamine, which inhibits the over-expressed Sonic Hedgehog pathway (i.e., a type of mutated signaling pathway). Other cytotoxic agents are also envisioned.

Figure 3:
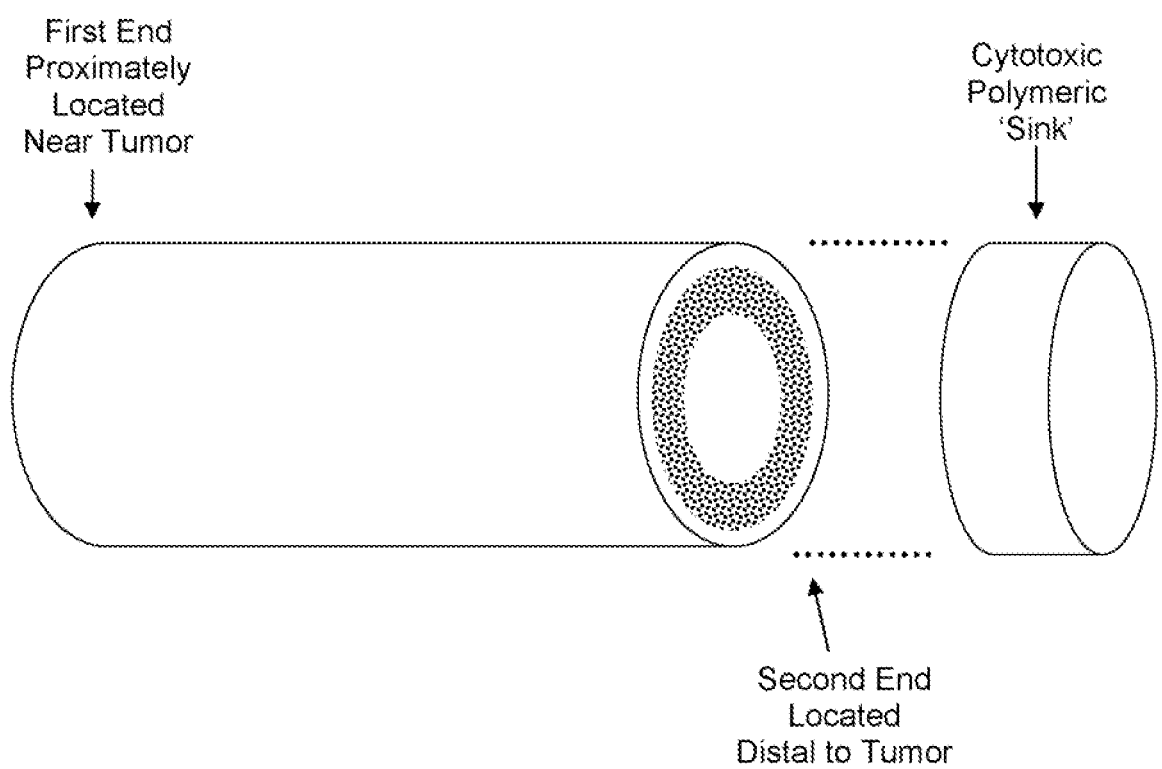
FIG. 3 is a perspective view of a schematic of an implantable system having a tubular conduit with a plurality of aligned nanofibers and a cytotoxic polymeric sink according to an embodiment.
Figure 4:
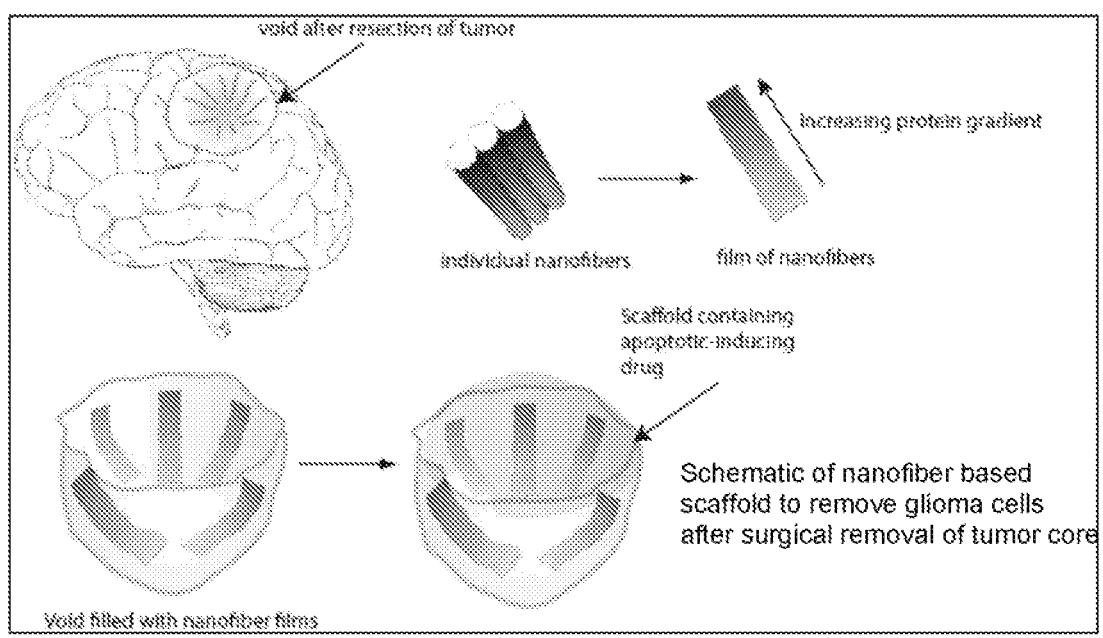
FIG. 4 is a schematic illustration of a method for treating a patient according to an embodiment.

As used herein, the polymeric 'sink' describes a portion of the implantable device designed, to receive tumor cells at a targeted secondary location remote from the primary tumor. As illustrated in FIG. 3, the polymeric sink desirably is disposed at, adjacent, or about a second end of the plurality of nanofibers distal to a first end of the plurality of nanofibers, the first end of the plurality of nanofibers being positioned into or substantially adjacent to at least a portion of the tumor. For example, a first end of the plurality of nanofibers may be disposed into or substantially adjacent to a tumor that is disposed in an inoperable area by using a catheter without risking the life of the patient. The plurality of nanofibers directs tumor migration to the polymeric 'sink', which is placed in a more accessible region for removal or surgical resection. Non-limiting examples of materials suitable for use as the polymeric sink include various polymeric and biopolymeric thin films, including PAN-MA, PVA, PMMA, chitosan, laminin, collagen, etc., or hydrogels, such as agarose, Matrigel, Neurogel, collagen, chitosan, or a composite of various hydrogels. In particular embodiments, the polymeric sink is disposed in a pouch made of a biocompatible material (e.g., that will not induce an immune response). Non-limiting examples of the pouch material include Teflon. The sink may be in communication with one or a plurality of implanted devices. One example of this is illustrated in FIG. 4.

The implantable devices provided herein desirably are quite durable and are capable of maintaining their integrity and topography upon implantation into a patient in need. Desirably, the implantable devices are sized and shaped such that they may be implanted using minimally invasive techniques. For example, in particular embodiments, a large-gauge needle, catheter, or trochar can be used to deploy the implantable device within the tumor with minimal disruption to the surrounding tissue. Alternatively, the implantable device may be implanted in an open surgical procedure.

The tumor cells that migrate to a secondary location from the primary tumor site by means of the implantable device may be dealt with using various methodologies. For example, in embodiments surgical resection can be used to remove the tumor cells from the secondary location which is more accessible than the primary tumor site. In other embodiments, a cytotoxic agent can be used in the polymeric sink to kill the tumor cells without requiring removal of the tumor cells. Thus, embodiments of the present description provide a novel and innovative method for treating malignancies, particularly those malignancies that are inoperable or inaccessible to delivery of cytotoxic agents.

The present description may be further understood with reference to the following non-limiting examples.

EXAMPLES

In Vitro Experiments
Fabrication and Characterization a Aligned Nanofiber Films for Tumor Cell Migration Slow degrading nanofibers films were fabricated from a poly(caprolactone) (PCL) polymer using a electrospinning processes known to those skilled in the art. The nanofiber films were coated with the extracellular matrix protein, laminin, to promote cell migration. Laminin has been shown to be in higher concentration at the periphery of the tumor core, suggesting that the protein may have a significant role in tumor cell migration.

Figure 5:
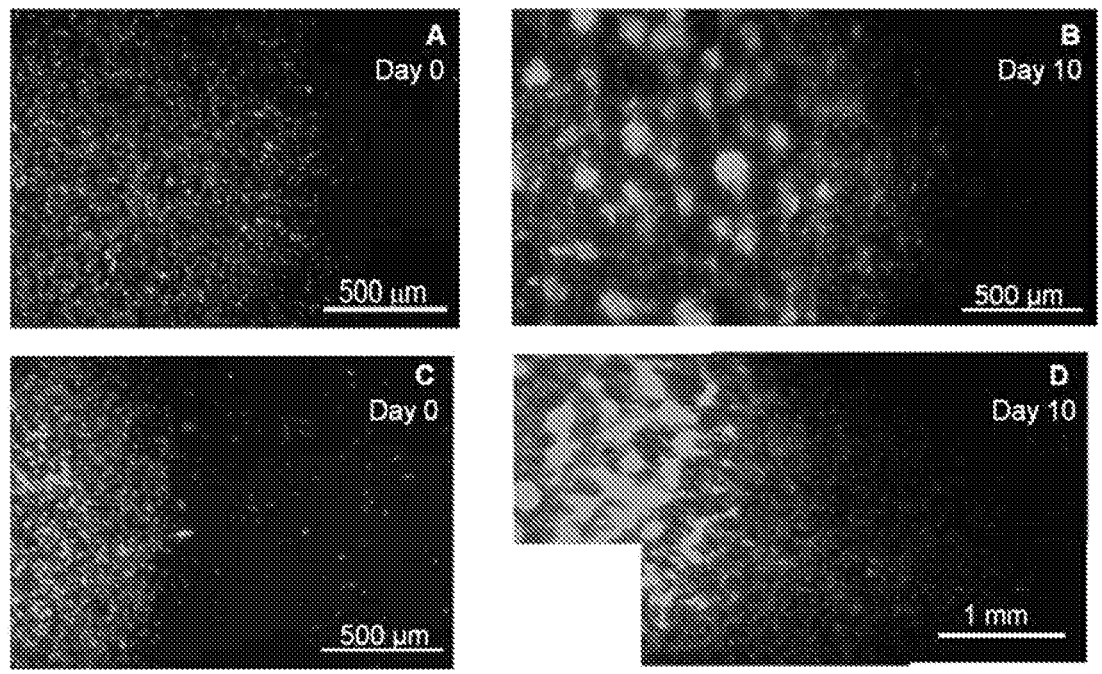
FIGS. 5A-5D are images of tumor cells seeded on a smooth film (A/B) or an aligned nanofiber film (C/D) taken 2 hours after seeding (A/C) or 10 days after seeding (B/D).
Figure 6:
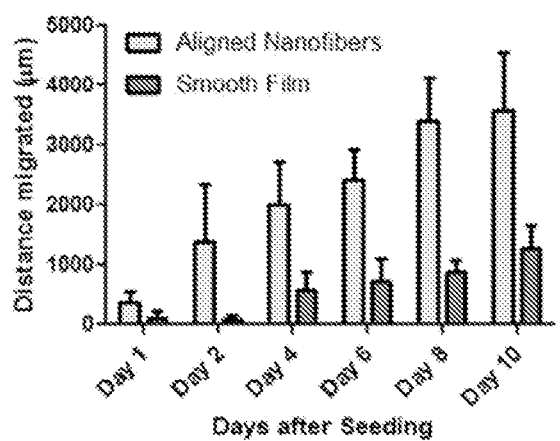
FIG. 6 is a graph illustrating the tumor cell migration of cells seeded on aligned nanofibers as compared to a smooth film.

To determine the effect of the topographical cues provided by the aligned nanofibers on tumor cell migration, an experiment was conducted to compare tumor cell migration on aligned nanofibers films to smooth films. The results, illustrated in FIGS. 5-6, demonstrate that the aligned, nanofiber films promoted significantly higher tumor cell migration as compared to the smooth films as evidenced by the distance of migration. (FIG. 5: tumor cells imaged 2 hours after seeding on a smooth film (A), tumor cells imaged 10 days after seeding on a smooth film (B), tumor cells imaged 2 hours after seecing on aligned nanofibers (C), and tumor cells imaged 10 days after seeding on aligned nanofibers (D); FIG. 6: quantitative analysis of tumor cell migration on the aligned nanofibers as compared to smooth film).

Fabrication and Characterization of Apoptotic Hydrogel Sink

The smoothened inhibitor, cyclopamine, was evaluated to determine the effective drug concentration required to induce apoptosis in tumor cells. The viability of the tumors cells was measured at different concentrations of cyclopamine. Healthy cells (e.g., neurons and glia) were not affected by exposure to the drug. However, the results suggested that the collagen hydrogel scaffold should be conjugated with 30 µM of cyclopamine.

A nanofiber film having a cytotoxic sink was prepared by conjugating the cyclopamine to the backbone of a collagen hydrogel. A crosslinker N,N'-carbonyldiimidazole was used to link the hydroxyl group on the cyclopamine with an amine group on the collagen. To verify whether the cyclopamine was conjugated to the collagen hydrogel, $C^{13}$ NMR was performed. Three conditions, cyclopamine, cyclopamine conjugated to collagen, and cyclopamine and collagen scaffold without the crosslinker were analyzed using $C^{13}$ NMR. A third condition was included to determine if indeed the cyclopamine was tethered to the hydrogel rather than entrapped by the collagen. Cyclopamine has four carbons that are involved in double bonds, which appear between 150 and 120 ppm. The four peaks for the four carbons in the double bonds in cyclopamine were present in the cyclopamine only spectra and in cyclopamine tethered to collagen; however, the peaks were absent when cyclopamine was mixed with the collagen hydrogel.

Figure 7:
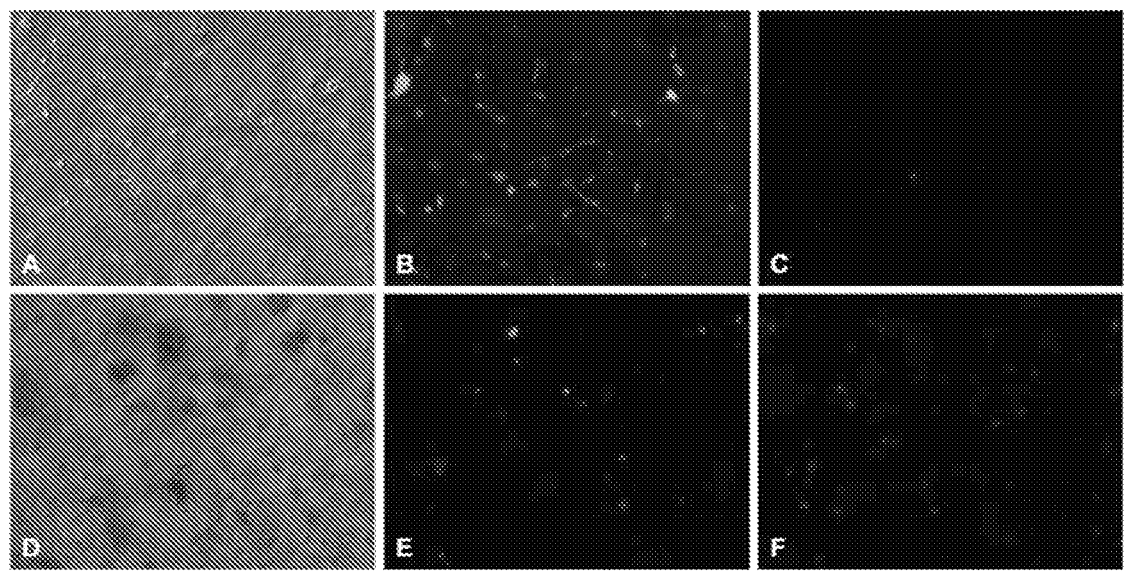
FIGS. 7A-7F are bright field and fluorescent images of tumor cells cultured with a cyclopamine conjugated collagen hydrogel 'sink' (A-C) and an apoptotic 'sink' (D-F).

Tumor cells were cultured within the cyclopamine conjugated collagen hydrogel sink to determine whether the bioactivity of cyclopamine was diminished and if the cells underwent apoptosis. As illustrated in FIG. 7, bright field and fluorescent images of the cells clearly underwent apoptosis when they were cultured in the apoptotic sink (D-F) as compared to a cyclopamine conjugated collagen hydrogel sink (A-C), (bright field images (A/D), live tumor cells stained with calcein (B/E), dead tumor cells stained with ethidium homodimer (C/F)). Notably, the number of dead cells in the cyclopamine conjugated collagen hydrogels was higher than the number of dead cells in the collagen only hydrogels.

Based on the foregoing in vitro experiments, it was determined that the tumor cells did indeed migrate further with topographical cues and that an apoptosis inducing sink may be effective to kill the tumor cells. Accordingly, preliminary in vivo experiments were conducted to evaluate the effectiveness of embodiments of the implantable scaffolds described herein at promoting directed tumor cell migration.

In Vivo Experiments

24 Rowett Nude Rats were inoculated with U87 mg-GFP cells, which is a human glioblastoma cell line. Seven days after the animals were inoculated with the tumor cells, 5 mm scaffolds were implanted into the brain near the tumor site. The tumors were inoculated 2 mm deep from the surface of the brain. The conduits were implanted 1.5 mm from the surface of the brain.

Figure 8:
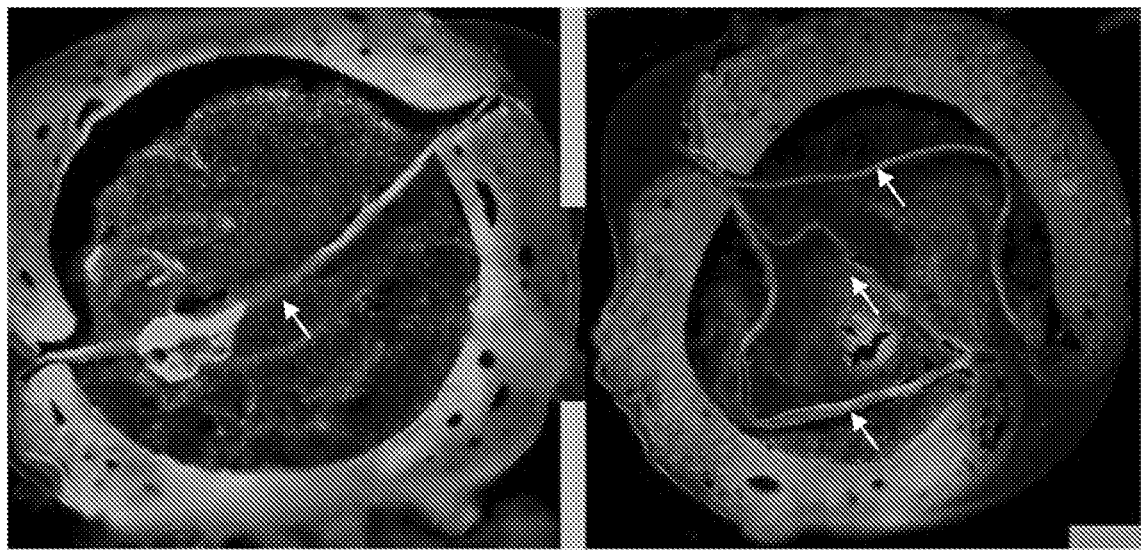
FIG. 8 is a sectioned image of a rat having a single scaffold implanted or three scaffolds implanted illustrating the ability of the scaffolds to promote the directional migration of the tumor cells through the scaffolds.

The scaffolds comprised a conduit, made of 10% polycaprolactone (PCL) and polyurethane. Within the conduit, PCL aligned nanofibers were inserted. Either a single scaffold or three scaffolds were implanted into the rats. The animals were perfused when they displayed symptoms from the tumors. From Day 16 to Day 18 after inoculation, the rats were perfused and the brains were dissected out with the scaffold. The scaffolds and brains were sectioned in a transverse orientation obtaining 50 μm sections. The sections were imaged after they had been sectioned. The tumor cells were visible due to their GFP expression. As illustrated in FIG. 8, the scaffolds were effective at promoting the directional migration of the tumor cells through the scaffolds.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

The invention claimed is:

1. A system comprising:
a first scaffold having a length and including a substrate film formed of aligned biocompatible polymeric nanofibers, the film having an elongated configuration with a length reaching from a first end portion to a second end portion remote from the first end portion, with the nanofibers oriented lengthwise of the film in uniaxial alignment with a longitudinal axis of the film, and further having cues for directing tumor cell migration lengthwise of the film from the first end portion to the second end portion, whereby the first scaffold is configured for directing tumor cell migration away from the first end portion of the film at a tumor site to a distal location of the second end portion of the film remote from the tumor site, the first scaffold being free of a cytotoxic agent;
a second scaffold that has a length less than the length of the first scaffold, is free of aligned biocompatible nanofibers, and is separate from the first scaffold and thereby configured for surgical implantation and resection separately from the first scaffold, adjacent the second end portion of the film, whereby the second scaffold is configured to receive tumor cells migrated from the first end portion of the film at a tumor site to the second end portion of the film at a distal location remote from the tumor site; and
a cytotoxic agent tethered or conjugated to the second scaffold to contact and kill the migrated tumor cells received at the second scaffold.

2. A system as defined in claim 1, wherein the first scaffold is one of a plurality of first scaffolds that are free of a cytotoxic agent and separate from one another, each of which has a length greater than the length of the second scaffold, includes a respective substrate film that is formed of aligned biocompatible polymeric nanofibers, has an elongated configuration with a length reaching from a first end portion to a second end portion remote from the first end portion, and has cues for directing tumor cell migration lengthwise from the first end portion to the second end portion, wherein the second scaffold is separate from the first scaffolds and configured to receive tumor cells migrated from the first end portion to the second end portion of each film.

3. A system as defined in claim 1, wherein the cues comprise topography features of the film.

4. A system as defined in claim 3, wherein the topography features comprise grooves.

5. A system as defined in claim 1 wherein greater than 50% of the nanofibers have uniaxial alignment within ±20 degrees of the longitudinal axis.

6. A system as defined in claim 1 wherein at least 60% of the nanofibers have uniaxial alignment within ±20 degrees of the longitudinal axis.

7. A system as defined in claim 1 wherein at least 75% of the nanofibers have uniaxial alignment within ±20 degrees of the longitudinal axis.

8. A system as defined in claim 1 wherein at least 85% of the nanofibers have uniaxial alignment within ±20 degrees of the longitudinal axis.

9. A system as defined in claim 1, wherein the first scaffold further includes a secondary structure containing the film.

10. A system as defined in claim 9, wherein the secondary structure comprises a tubular conduit.

11. A system as defined in claim 9, wherein the secondary structure is configured to shield healthy tissue from tumor cells migrating along the film.

12. A system as defined in claim 9, wherein the secondary structure is formed of material comprising a biodegradable polymer.

13. A system as defined in claim 1, wherein the length of the film is within a range of 2 to 100 millimeters.

* * * * *